United States Patent
Taskiran et al.

(10) Patent No.: US 7,047,086 B2
(45) Date of Patent: May 16, 2006

(54) SINGLE ELECTRODE PROBE FOR A CARDIAC PACEMAKER SYSTEM

(75) Inventors: Murat Taskiran, Erlangen (DE); Erhard Flach, Berlin (DE); Max Schaldach, deceased, late of Erlangen (DE); by Max Schaldach, Jr., legal representative, Berlin (DE)

(73) Assignee: BIOTRONIK Mess-und Therapiegerä te GmbH & Co. Ingenieurbü ro, Berlin (DE)

( * ) Notice: Subject to any disclaimer, the term of this patent is extended or adjusted under 35 U.S.C. 154(b) by 496 days.

(21) Appl. No.: 10/224,528

(22) Filed: Aug. 20, 2002

(65) Prior Publication Data

US 2003/0040786 A1   Feb. 27, 2003

(30) Foreign Application Priority Data

Aug. 23, 2001  (DE)  ................ 101 42 834

(51) Int. Cl.
*A61N 1/05* (2006.01)

(52) U.S. Cl. ............... 607/126; 607/125; 607/122; 600/375; 600/393

(58) Field of Classification Search ............... 607/122, 607/123, 125, 126, 128; 600/373, 374, 375, 600/393
See application file for complete search history.

(56) References Cited

U.S. PATENT DOCUMENTS

| | | | |
|---|---|---|---|
| 4,154,247 A | 5/1979 | O'Neill | |
| 4,660,571 A * | 4/1987 | Hess et al. | 607/116 |
| 4,706,671 A * | 11/1987 | Weinrib | 606/159 |
| 4,726,379 A * | 2/1988 | Altman et al. | 607/9 |
| 4,917,104 A * | 4/1990 | Rebell | 600/585 |
| 5,555,883 A * | 9/1996 | Avitall | 600/374 |
| 5,674,274 A * | 10/1997 | Morgan et al. | 607/123 |
| 5,769,077 A | 6/1998 | Lindegren | |
| 5,782,239 A | 7/1998 | Webster | |
| 5,836,947 A * | 11/1998 | Fleischman et al. | 606/47 |
| 6,071,282 A * | 6/2000 | Fleischman | 606/41 |
| 6,076,019 A | 6/2000 | Rutten | |
| 6,500,185 B1 * | 12/2002 | Mathews et al. | 606/159 |

FOREIGN PATENT DOCUMENTS

| | | |
|---|---|---|
| DE | 41 08 269 C1 | 6/1992 |
| EP | 0 009 732 A1 | 4/1980 |
| EP | 0 426 089 A2 | 5/1991 |
| EP | 0 783 900 A2 | 12/1996 |
| EP | 0 779 079 A1 | 6/1997 |
| EP | 0 788 808 A2 | 8/1997 |
| FR | 27137492 A1 | 6/1995 |
| WO | WO 00/76570 A2 | 12/2000 |

* cited by examiner

*Primary Examiner*—Kennedy Schaetzle
(74) *Attorney, Agent, or Firm*—Hahn Loeser & Parks LLP

(57) ABSTRACT

A single electrode probe for a cardiac pacemaker system, in particular for a DDD cardiac pacemaker system, has an electrode line with a bifurcated section, at the beginning of which the electrode line divides into two electrode line portions which rejoin at the end of the section to again form one portion, wherein at least one of the portions has at least one electrode for the delivery of electrical energy to adjoining myocardium.

2 Claims, 3 Drawing Sheets

SINGLE ELECTRODE PROBE FOR A CARDIAC PACEMAKER SYSTEM

The invention concerns a single electrode probe for a cardiac pacemaker system, in particular for a DDD cardiac pacemaker system, comprising an electrode line which has a section which is divided into two and at the beginning of which an electrode line portion is divided into two portions which join again at the end of the section to form one portion, wherein at least one of the portions has at least one electrode for the delivery of electrical energy to adjoining myocardium.

BACKGROUND OF THE ART

In accordance with knowledge in the cardiac pacemaker art, the use of so-called DDD cardiac pacemaker systems is recommended in relation to appropriate pathological results. That specification "DDD" (Dual pacing/Dual sensing/Demand+Triggered) means that on the one hand stimulation ("pacing") is effected in both heart chambers and that, on the other hand, innate actions in respect of the sinus or AV node of the heart, which are still present, are detected both in the atrium and also in the ventricle ("sensing"). So-called "double lead" DDD pacemaker systems are already known for that purpose. The main disadvantages thereof however is that two separate electrode probes have to be implanted into the heart and positioned there.

Single probes are also known in which a ventricular electrode is arranged at the probe tip and two atrial ring electrodes are arranged at a corresponding distance from the ventricle electrode on the probe body. The atrial ring electrodes are used to detect the atrial potential, whereby ventricular stimulation is triggered after a suitable atrio-ventricular delay. Ventricular stimulation can be effected in bipolar manner. In principle it is admittedly possible for the above-discussed single electrode probe also to be used for DDD cardiac pacemaker systems. A problem which arises here however is that the atrial ring electrodes are not placed in an established position on the wall but float freely in the blood stream. These so-called "floating" electrodes in the atrium result in serious limitations in terms of the stimulation properties as generally very high stimulation amplitudes have to be used. The main reason for this is the lack of on-wall established placement of the floating electrodes. The high stimulation amplitudes entail the disadvantage of a high level of energy consumption and frequent phrenic stimulation effects.

In comparison, published European Patent application 0 779 079, by Boehm and Bolz, discloses a single electrode probe (referred to as a single lead) which, on the part of its length which in the implanted condition is placed in the atrium, is of such a shape that at least one atrial electrode— usually a ring electrode—of the probe can be caused to bear in an established position against the wall of the atrium of the heart. In order to achieve that the probe is provided over that part of its length with an elastic pre-shaping element which imparts to the probe there a definedly deflected shape. By virtue of its elasticity however the pre-shaping element can be transferred from its defined configuration into a substantially straight stretched condition, which is effected by means of the usual guide wire used in the probe implantation operation. It will be appreciated that in that respect the guide wire must be significantly stiffer in regard to its elasticity properties than the pre-shaping element.

In the implantation procedure prior to implantation of the probe the guide wire is advanced until it comes to a stop against the tip of the probe, in which case that advance movement of the guide wire causes the application to the probe body of a pulling force which results in stretching of the probe in the region of the pre-shaping element. The probe can then be introduced into the heart in that stretched condition. After implantation of the probe and withdrawal of the guide wire the probe is then so designed over the above-mentioned part of its length by virtue of its pre-shaping element that the probe bears with at least one atrial ring electrode against the wall of the atrium of the heart. The relatively complicated configuration of that single electrode probe is found to be a disadvantage in that respect. In addition using a guide wire in implantation of the single electrode probe is not desirable.

Published European Patent application EP 0 426 089, by Cohen and Thacker, discloses an electrode arrangement with two separate electrode probes, wherein one of the electrode probes is introduced into the atrium and further into the ventricle, while the other electrode probe is fitted as a counter-electrode externally to the heart, that is to say as an endocardial counter-electrode. Provided at the distal end of the electrode line is a helix electrode 25 as a tip electrode which is fixed in the right ventricular myocardium by virtue of being screwed therein. Above the tip electrode a section of the line is divided into two, wherein both portions of the divided section each have a respective coil electrode 22, 24 for defibrillation purposes. The two branches are biased relative to each other so that they are arranged in mutually spaced relationship in the implanted condition. In this case the electrodes 22, 24 are intended to form a contact with the right ventricular myocardium. The two-part electrode line and the electrodes 22, 24 were selected here in order, with the endocardial electrodes 18, 20, to form a quadrilateral polygon (orthogonal electrode placement). A disadvantage in this arrangement however is that two separate electrode probes have to be implanted. In addition the electrode line is adequately fixed only in the ventricle so that the electrodes in the atrium are in the form of floating electrodes. Electrical contact of the tip electrode in the ventricle can readily be ensured while the electrical contact in the atrium can be critical and thus suffers from the above-discussed disadvantages. In addition, the prerequisites for fixing electrodes in the atrium are different from those involved in fixing electrodes in the ventricle as the atrium essentially involves a "passageway".

U.S. Pat. No. 4,154,247, to O'Neill, has a FIG. 4f that shows an electrode line with a branched section 620 that, as illustrated in the Figure, is intended for placement in the ventricle but which in accordance with the description can also be placed in the atrium of the heart. This patent, however, says nothing in regard to fixing the electrode line.

The object of the invention is to provide an electrode line to be fixed in the atrium of a heart.

SUMMARY OF THE INVENTION

In accordance with the invention that object is attained by a single electrode probe of the kind set forth in the opening part of this specification, in which the section which is divided into two is arranged on the electrode line and is of such a configuration as to afford the electrode line in the implanted condition a hold in the atrium of a heart.

A section of the electrode line, which is divided into two in that way, contributes substantially to improving the hold of electrodes to the atrial myocardium without in that respect substantially complicating the design configuration of the electrode line.

In a further embodiment of the invention two ring electrodes are arranged at each of the respective portions of the two-part section of the electrode line.

In a preferred embodiment of the invention the two portions of the two-part section of the electrode line extend in mutually parallel relationship and are pre-shaped in such a way that they are curved convexly outwardly in order in the implanted condition to be pressed in diametrally opposite relationship together with the ring electrodes against the atrial myocardium.

In a further embodiment of the invention at least one ring electrode is provided only at one of the two portions of the two-part section.

A further alternative configuration involves an electrode line which has a stiffening coil of elastic material, which is formed in a plurality of turns. Provided in the lumen of that electrode line is a cord or string which is fixed with its distal end to the electrode line. Pulling on the cord in that way affords an upsetting force in the electrode line. The coil is designed in such a way that when a pulling force is applied to the cord the electrode line bends out of its longitudinal direction and assumes a predetermined three-dimensional shape. When using suitable materials it is possible to fix that shape so that the electrode line retains the three-dimensional deformation when the pulling force by way of the cord is relaxed. Such a design configuration of the electrode line can be provided alternatively to or in addition to the above-mentioned pre-shaping of the electrode line. A clamping or crimping can be provided for fixing the cord under tension for example in the region of an electrode plug, at the proximal end of the electrode line. The cord is accordingly pulled or tightened after implantation of the electrode line and fixed in the pulled condition in the region of the electrode plug. It is possible to achieve greater curvature forces with an electrode line of that kind, than with an electrode line which is only pre-shaped.

Another embodiment is distinguished by a memory metal element in the region of the electrode line to be deformed, which element for example involves a per se known titanium alloy which, when a triggering temperature is exceeded, changes its shape from a first shape to a second shape. The memory metal element is designed in such a way that its first shape corresponds to a substantially stretched electrode line which permits the electrode line to be easily introduced while the second shape of the memory metal results in an electrode line which is deformed in accordance with the invention, after the triggering temperature is exceeded. Advantageously a heating element can be provided for heating the memory metal element to the triggering temperature, if body temperature is not sufficient to achieve the triggering temperature. If body temperature is sufficient to achieve the triggering temperature at which the memory metal changes its shape, it is possible to provide cooling means or alternatively the electrode lines can also be introduced in a cooled condition so that it slowly warms up during and after introduction into the blood vessel and finally reaches the triggering temperature.

BRIEF DESCRIPTION OF THE DRAWINGS

The invention will now be described in greater detail by means of embodiments by way of example with reference to the Figures in which.

DETAILED DESCRIPTION OF A PREFERRED EMBODIMENT

Figure 1:
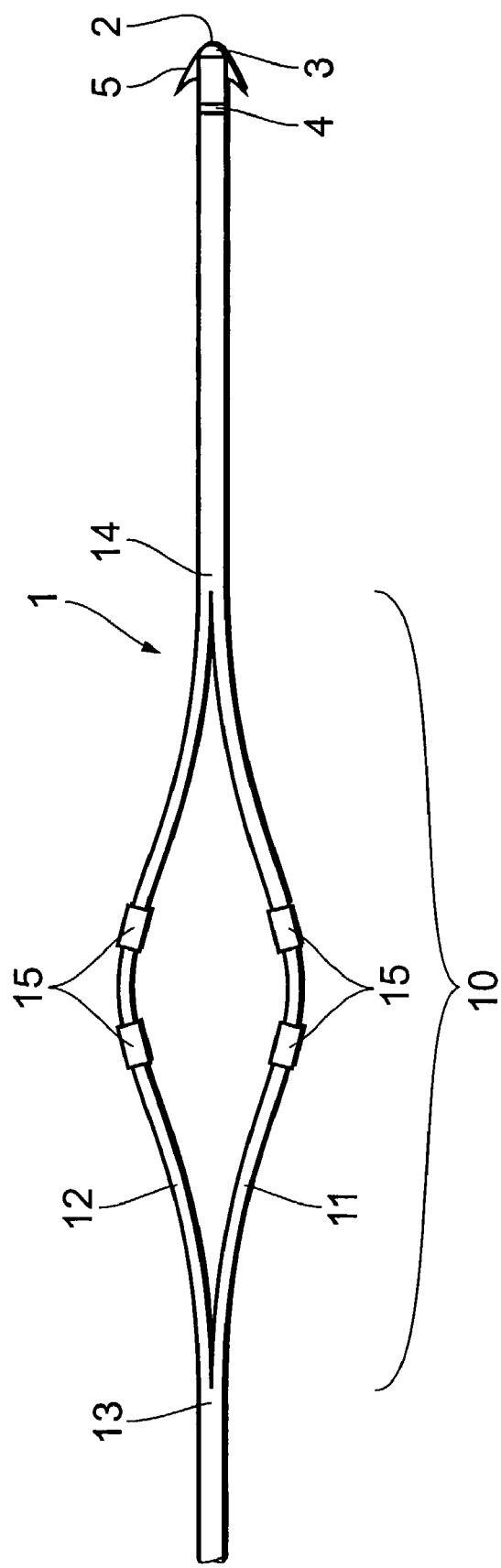
FIG. 1 shows a distal end of an electrode line, which is intended for placement in the heart.

FIG. 1 shows that section of a single lead electrode line 1 which is intended for placement in a heart. A distal end 2 of the electrode line 1 and the section of the electrode line 1, which is immediately adjoining same, are provided for placement in a ventricle of a heart. For that purpose the electrode line 1 has a tip electrode 3, a ring electrode 4 disposed in the proximity of the tip electrode and so-called tines 5 for anchoring the electrode line in the myocardium of the ventricle.

The distal section of the electrode line 1 that is provided for placement in the ventricle is adjoined by a section 10 that is provided for placement in the atrium of a heart. In the region of the section 10, the electrode line 1 is divided into two portions 11 and 12. The two portions 11 and 12 are joined at a proximal end 13 of the two-part section 10 to form a single electrode line which for example leads to an implantable pacemaker. At the distal end 14 of the two-part section 10 the two portions 11 and 12 are joined to form that distal section of the electrode line 1, which is designed to be arranged in the ventricle.

The two portions 11 and 12 each carry two ring electrodes 15 which are to serve for stimulation of the myocardium in the region of the atrium.

Figure 2:
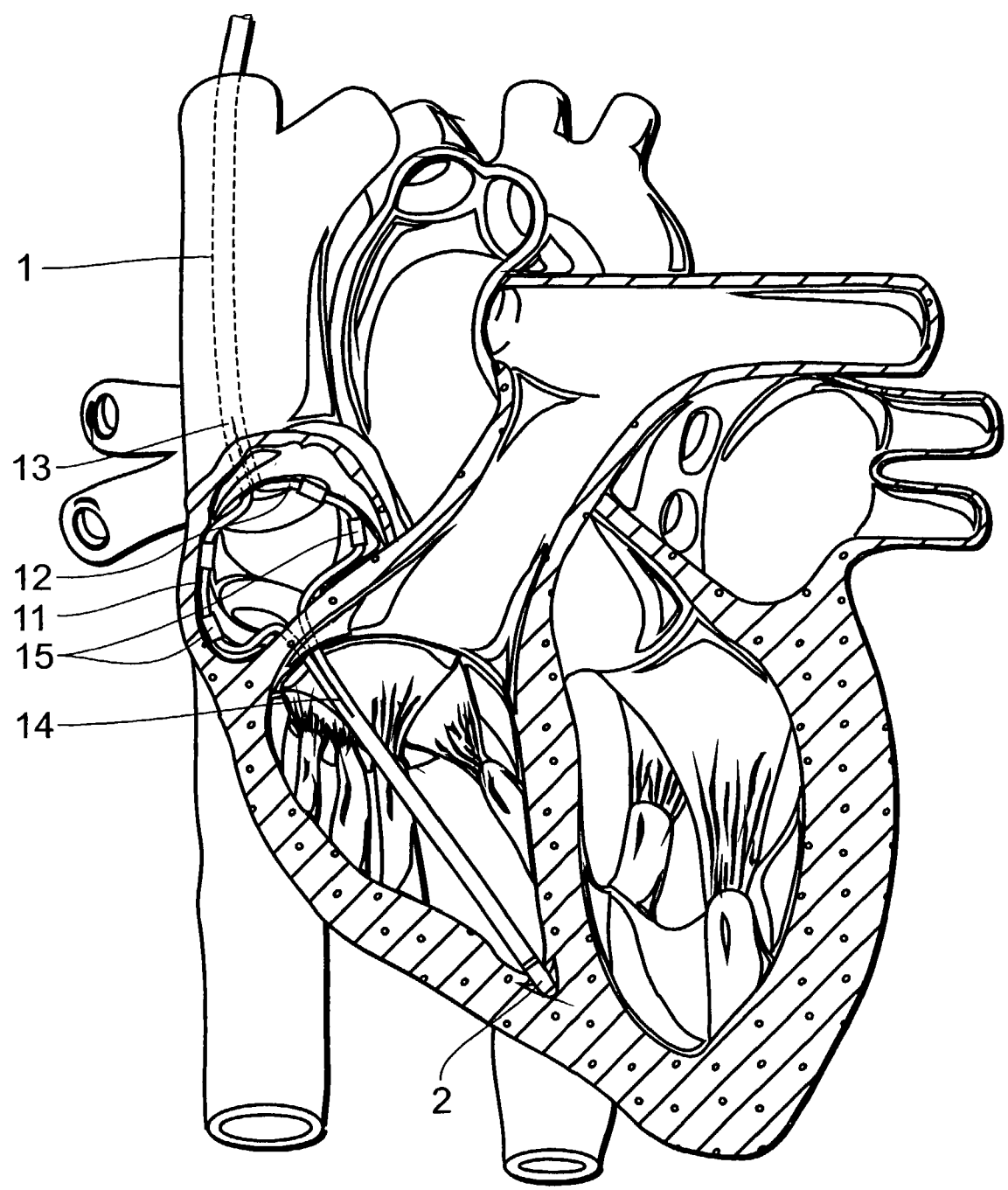
FIG. 2 shows the section of the electrode line illustrated in FIG. 1, placed in a heart.

The two portions 11 and 12 are biased relative to each other in such a way that in the implanted condition, in particular in the region of the electrodes 15, they are pressed against diametrically oppositely disposed walls of the atrium, as is shown in FIG. 2. In the implanted condition the two portions 11 and 12 of the electrode line 1 are convexly outwardly curved—apart from the transitional regions at 13 and 14—in order to ensure good electrical contact of the ring electrodes 15 with the atrial myocardium and at the same time to fix the electrode line 1 in the atrium solely by virtue of the pre-shaping.

In contrast to the fixing options for fixing an electrode line in the ventricle which for example can be fixed by means of a tip electrode to the ventricular myocardium, that is not possible in the atrium as the atrium is essentially a "passageway". Fixing to the atrial myocardium is not possible by means of a tip electrode as the electrode line is only introduced through the atrium into the ventricle.

The good holding function for the two-part section of the electrode line to the atrial myocardium and thus good electrical contact of the ring electrodes 15 on the two portions 11 and 12 with the atrial myocardium is implemented by the outwardly curved portions 11 and 12 which are braced against the diametrally oppositely disposed points in the atrium, by virtue of their mutual biasing effect. In that respect the elasticity properties of the portions 11 and 12 are so selected as to ensure that electrical contact of the electrodes 15 with the atrial myocardium is durably guaranteed.

As an alternative to the above-described embodiment the section of the electrode line which is divided into two can also be designed in such a way that one or more electrodes 15 are provided only on one of the two portions 11 and 12.

FIGS. 3a through d show a detail view of an alternative embodiment of the electrode line which can be introduced into the atrium of the heart in a stretched shape and which can assume its shape according to the invention after having been introduced.

The electrode line section 10 in FIG. 3 includes a casing 30 (only indicated in FIG. 3a) and within the casing 30 a metal coil 32 and a cord or string 34 which is arranged in a lumen enclosed by the metal coil 32 and which is connected at its distal end to the metal coil 32 by way of a connecting plate 36.

Figure 3B:
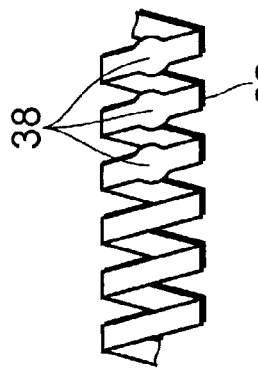
FIGS. 3a through d show a design detail of an electrode line which is deformable by upsetting a stiffening coil.
Figure 3C:
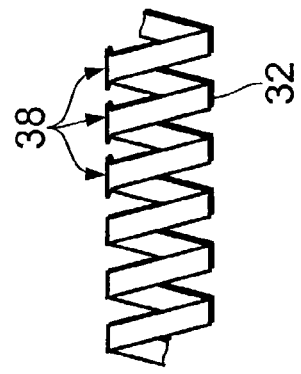
Figure 3D:
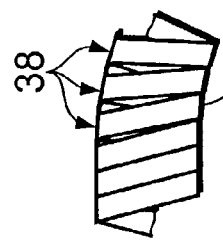
Figure 3A:
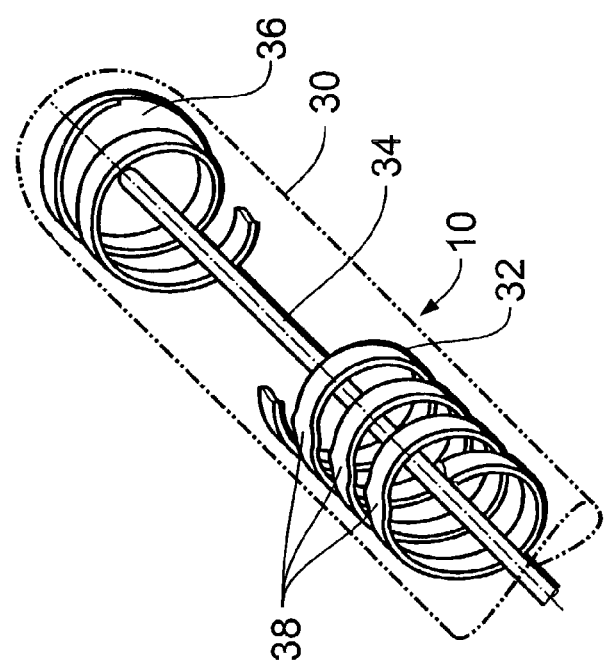

FIG. 3b shows a plan view of a part of the metal coil 32 while FIG. 3c shows a side view of the part of the metal coil 32. It will be seen that the individual turns of the metal coil 32 are spaced from each other and that the strip material that constitutes the metal coil 32 is wider at each of the locations 38. By applying a pulling force to the cord 34 the metal coil 32 is shortened until the turns of the metal coil 32 bear against each other; see FIG. 3d. As the strip material of the metal coil 32 is widened at each of the locations 38 the shortened or upset metal coil 32 does not retain its elongated stretched shape but assumes the flexed configuration shown in FIG. 3d. On the basis of the principle shown in FIG. 3 the coils can be so designed, in a manner corresponding to the metal coil 32, that an electrode line assumes any three-dimensional curvatures, by the application of a pulling force to a cord fitted therein. Without a pulling force on the cord the electrode line is stretched and flexurally soft and can be easily introduced into the blood vessel, as is shown in FIG. 3a.

A single electrode probe like that illustrated usually has an electrode plug (not shown here) at its proximal end for connecting the electrode line to a therapy device such as a cardiac pacemaker. A clamping means or crimping can be provided for example in the region of such an electrode plug for fixing the cord under tension. The electrode plug correspondingly preferably has a clamp or crimping device. The cord is accordingly pulled or tightened after implantation of the electrode line and fixed in the tightened condition in the region of the electrode plug.

What is claimed is:

1. A single electrode probe for a cardiac pacemaker system, in particular for a DDD cardiac pacemaker system, the probe comprising:

an electrode line having a bifurcated section along a length thereof wherein the bifurcated section comprises a first and a second electrode line portion that separate at a beginning of the bifurcated section and rejoin at an end of the bifurcated section, such that at least one of the electrode line portions has at least one electrode for the delivery of electrical energy to adjoining myocardium, and wherein the bifurcated section is arranged and designed to afford the electrode line a hold in the atrium of a heart when in an implanted condition, and wherein the electrode line comprises a casing which encloses a stiffening coil of elastic material which is formed by a plurality of turns and which in turn encloses a lumen, and wherein a cord is arranged in the lumen and is fixed with a distal end thereof to the stiffening coil, such that a force which acts in a longitudinal direction of the electrode line and which upsets at least a section thereof can be produced in the electrode line and the elastic material forming the turns of the coil is so shaped that the electrode line is three-dimensionally deformed when the cord is tightened and the upsetting force is operative.

2. A single electrode probe for a cardiac pacemaker system, in particular for a DDD cardiac pacemaker system, the probe comprising:

an electrode line having a bifurcated section along a length thereof;

the bifurcated section comprising a first and a second electrode line portion that separate at a beginning of the bifurcated section and rejoin at an end of the bifurcated section, such that each of the electrode line portions has exactly two ring electrodes for the delivery of electrical energy to adjoining myocardium;

wherein the bifurcated section is arranged and designed to afford the electrode line a hold in the atrium of a heart when in an implanted condition, and wherein the electrode line comprises a casing which encloses a stiffening coil of elastic material which is formed by a plurality of turns and which in turn encloses a lumen, and wherein a cord is arranged in the lumen and is fixed with a distal end thereof to the stiffening coil, such that a force which acts in a longitudinal direction of the electrode line and which upsets at least a section thereof can be produced in the electrode line and the elastic material forming the turns of the coil is so shaped that the electrode line is three-dimensionally deformed when the cord is tightened and the upsetting force is operative.

* * * * *